United States Patent
Zucker et al.

(10) Patent No.: US 12,178,663 B2
(45) Date of Patent: Dec. 31, 2024

(54) SYSTEMS, DEVICES, AND METHODS FOR MONITORING A ROD REDUCTION PROCESS

(71) Applicant: Mazor Robotics Ltd., Caesarea (IL)

(72) Inventors: Ido Zucker, Tel-Aviv (IL); Yonatan Ushpizin, Glil Yam (IL); Eliyahu Zehavi, Tel-Aviv (IL)

(73) Assignee: Mazor Robotics Ltd., Caesarea (IL)

( * ) Notice: Subject to any disclaimer, the term of this patent is extended or adjusted under 35 U.S.C. 154(b) by 265 days.

(21) Appl. No.: 17/526,873

(22) Filed: Nov. 15, 2021

(65) Prior Publication Data

US 2022/0192773 A1 Jun. 23, 2022

Related U.S. Application Data

(60) Provisional application No. 63/126,962, filed on Dec. 17, 2020.

(51) Int. Cl.
*A61B 90/00* (2016.01)
*A61B 17/70* (2006.01)
*A61B 34/10* (2016.01)
*A61B 34/20* (2016.01)
*A61B 34/30* (2016.01)
*A61B 17/56* (2006.01)

(52) U.S. Cl.
CPC .......... *A61B 90/06* (2016.02); *A61B 17/7086* (2013.01); *A61B 34/10* (2016.02); *A61B 34/30* (2016.02); *A61B 2017/564* (2013.01); *A61B 17/7001* (2013.01); *A61B 34/20* (2016.02); *A61B 2090/066* (2016.02)

(58) Field of Classification Search
CPC ............................ A61B 17/7083–7089; A61B 34/30–2034/306; A61B 34/10–2034/108; A61B 34/20–2034/258; A61B 90/06–2090/066
See application file for complete search history.

(56) References Cited

U.S. PATENT DOCUMENTS

| | | | |
|---|---|---|---|
| 8,202,274 B2 | 6/2012 | McLean |
| 8,303,595 B2 | 11/2012 | Jones |
| 8,551,092 B2 | 10/2013 | Morgan et al. |
| 8,979,848 B2 | 3/2015 | Butters et al. |
| 9,451,919 B2 | 9/2016 | Roche |
| 9,585,700 B2 | 3/2017 | Wehrle et al. |
| 9,867,706 B2 | 1/2018 | Bonutti |

(Continued)

FOREIGN PATENT DOCUMENTS

| | | |
|---|---|---|
| CA | 2170275 | 1/2006 |

OTHER PUBLICATIONS

Extended Search Report for European Patent Application No. 21213992.7, dated May 16, 2022, 9 pages.

*Primary Examiner* — Julianna N Harvey
(74) *Attorney, Agent, or Firm* — Sheridan Ross P.C.

(57) ABSTRACT

Methods and systems for monitoring a rod reduction process is provided. The methods and systems include determining, based on at least one parameter, a threshold for forces exerted by a tool on a rod or a pedicle screw and receiving data corresponding to a magnitude of the forces exerted by the tool on the pedicle screw or the rod during reduction of the rod into a head of the pedicle screw. A surgical plan may be updated when the monitored magnitude meets the threshold.

18 Claims, 3 Drawing Sheets

(56) References Cited

U.S. PATENT DOCUMENTS

| | | | |
|---|---|---|---|
| 10,485,590 B2 | 11/2019 | Min et al. | |
| 10,512,490 B2 | 12/2019 | Carl et al. | |
| 10,524,843 B2 | 1/2020 | Mladenov et al. | |
| 2013/0072982 A1* | 3/2013 | Simonson | A61B 17/7083 606/267 |
| 2015/0230836 A1* | 8/2015 | Cochran | A61B 17/7032 606/86 A |
| 2017/0196508 A1 | 7/2017 | Hunter | |
| 2017/0325914 A1* | 11/2017 | Tushtev | A61B 17/866 |
| 2018/0325608 A1* | 11/2018 | Kang | A61B 34/71 |
| 2019/0059959 A1 | 2/2019 | Serra et al. | |
| 2019/0117280 A1 | 4/2019 | Avidano et al. | |
| 2020/0229858 A1 | 7/2020 | Haiat et al. | |
| 2021/0393337 A1 | 12/2021 | Zucker | |

\* cited by examiner

SYSTEMS, DEVICES, AND METHODS FOR MONITORING A ROD REDUCTION PROCESS

CROSS REFERENCE TO RELATED APPLICATIONS

This application claims the benefit of U.S. Provisional Application No. 63/126,962, filed on Dec. 17, 2020, and entitled "Systems, Devices, and Methods for Monitoring a Rod Reduction Process", which application is incorporated herein by reference in its entirety.

FIELD

The present technology is related generally to a rod reduction process, and more particularly, to monitoring and adjusting a rod reduction process.

BACKGROUND

During some spinal procedures, pedicle screws may be implanted into a plurality of vertebrae and connected to each other via a rod. The rod may be inserted into a head or an extension of each screw and reduced onto each screw until the rod is secured in place. During the process, the rod may be adjusted to align with the pedicle screws.

SUMMARY

Example aspects of the present disclosure include:

A system for monitoring a rod reduction process according to at least one embodiment of the present disclosure comprises: a tool configured to reduce a rod into a head of a pedicle screw; at least one sensor configured to measure forces or torques exerted on the pedicle screw; at least one processor; and at least one memory storing instructions for execution by the at least one processor that, when executed, cause the at least one processor to: determine, based on at least one parameter, a threshold for forces or torques exerted by the tool on the rod or the pedicle screw; and receive, from the at least one sensor, data corresponding to a magnitude of the forces or torques exerted by the tool on the pedicle screw or the rod during reduction of the rod into the head by the tool.

Any of the aspects herein, wherein the tool is handheld and operated by a user.

Any of the aspects herein, wherein the at least one sensor is disposed on at least one of a tool or the head of the pedicle screw.

Any of the aspects herein, wherein the at least one sensor is disposed on the tool and is integrated into the tool.

Any of the aspects herein, wherein the at least one parameter is at least one of a screw quality, a geometry of the rod, a mechanical property of the rod, a patient range of motion, a bone quality, or a preoperative plan.

Any of the aspects herein, wherein the memory stores additional instructions for execution by the at least one processor that, when executed, further cause the at least one processor to: update a plan for reducing the rod when the monitored magnitude meets the threshold.

Any of the aspects herein, further comprising: at least one robotic arm configured to selectively implant the pedicle screw in a patient and hold the tool; and at least one robotic sensor disposed on the robotic arm, wherein the memory stores additional instructions for execution by the at least one processor that, when executed, further cause the at least one processor to: receive, from the at least one robotic sensor, sensor data corresponding to a force or torque exerted by the robotic arm onto the pedicle screw during implantation of the pedicle screw in the patient; and determine a screw quality of the pedicle screw based on the sensor data.

Any of the aspects herein, wherein the memory stores additional instructions for execution by the at least one processor that, when executed, further cause the at least one processor to: cause the robotic arm to insert the rod into the patient.

Any of the aspects herein, wherein the memory stores additional instructions for execution by the at least one processor that, when executed, further cause the at least one processor to: cause the robotic arm to operate the tool to reduce the rod onto a plurality of pedicle screws in stages, the plurality of pedicle screws including the pedicle screw.

Any of the aspects herein, wherein reducing the rod in stages comprises causing the robotic arm to incrementally tighten, in sequence, a set screw in a head of each pedicle screw of the plurality of pedicle screws, to avoid point loading any single pedicle screw.

Any of the aspects herein, wherein the tool is a persuader.

A device for monitoring a rod reduction process according to at least one embodiment of the present disclosure comprises: at least one processor; and at least one memory storing instructions for execution by the at least one processor that, when executed, cause the at least one processor to: determine a threshold, based on at least one parameter, for a force or torque exerted by a rod reduction tool during reduction of a rod into a head of each of one or more screws; and receive, from at least one sensor, data corresponding to a magnitude of the forces or torques exerted by the tool on the one or more screws or the rod during reduction of the rod into the head.

Any of the aspects herein, wherein the tool is handheld and operated by a user.

Any of the aspects herein, wherein the at least one parameter is at least one of a screw quality, a geometry of the rod, a mechanical property of the rod, a patient range of motion, a bone quality, or a preoperative plan.

Any of the aspects herein, wherein the memory stores additional instructions for execution by the at least one processor that, when executed, further cause the at least one processor to: update a plan for reducing the rod when the monitored magnitude meets the threshold.

Any of the aspects herein, wherein the memory stores additional instructions for execution by the at least one processor that, when executed, further cause the at least one processor to: receive, from the at least one robotic sensor, sensor data corresponding to a force or torque exerted by the robotic arm onto the pedicle screw during implantation of the pedicle screw in the patient; and determine a screw quality of the pedicle screw based on the sensor data.

Any of the aspects herein, wherein the memory stores additional instructions for execution by the at least one processor that, when executed, further cause the at least one processor to: cause the robotic arm to insert the rod into the patient.

Any of the aspects herein, wherein the memory stores additional instructions for execution by the at least one processor that, when executed, further cause the at least one processor to: cause the robotic arm to operate the tool to reduce the rod onto a plurality of pedicle screws in stages, the plurality of pedicle screws including the pedicle screw.

Any of the aspects herein, wherein reducing the rod in stages comprises causing the robotic arm to incrementally tighten, in sequence, a set screw in a head of each pedicle screw of the plurality of pedicle screws, to avoid point loading any single pedicle screw.

Any of the aspects herein, wherein the tool is a persuader.

A method for monitoring a rod reduction process according to at least one embodiment of the present disclosure comprises receiving a surgical plan for reducing a rod; determining, based on at least one parameter, a threshold for forces exerted by a tool on the rod or a pedicle screw; receiving data corresponding to a magnitude of the forces exerted by the tool on the pedicle screw or the rod during reduction of the rod into the head; and updating the plan when the monitored magnitude meets the threshold.

Any of the aspects herein, further comprising: causing the rod to be inserted into a patient; and causing the rod to be reduced onto a plurality of pedicle screws in stages using the tool, the plurality of pedicle screws including the pedicle screw.

Any of the aspects herein, wherein the tool is handheld and operated by a user.

Any of the aspects herein, further comprising: causing a robotic arm to insert the rod into a patient; and causing the robotic arm to operate the tool to reduce the rod onto a plurality of pedicle screws in stages, the plurality of pedicle screws including the pedicle screw.

Any of the aspects herein, wherein the at least one parameter is at least one of a property of each screw, a geometry of the rod, a mechanical property of the rod, a patient range of motion, bone quality, and/or a preoperative plan, and wherein the method further comprises: receiving, from at least one robotic sensor, sensor data corresponding to a force or torque exerted by the robotic arm onto the pedicle screw during implantation of the pedicle screw in a patient; and determining a screw quality of the pedicle screw based on the sensor data.

Any of the aspects herein, wherein updating the plan includes one or more of updating one or more surgical steps, removing one or more surgical steps, adding one or more surgical steps, updating a pose of the pedicle screw, updating a rod shape, updating a rod trajectory, or updating a rod insertion point.

Any of the aspects herein, wherein updating the plan includes modifying one or more surgical steps to move the tool from pedicle screw to pedicle screw to distribute the force or torque loads.

Any aspect in combination with any one or more other aspects.

Any one or more of the features disclosed herein.

Any one or more of the features as substantially disclosed herein.

Any one or more of the features as substantially disclosed herein in combination with any one or more other features as substantially disclosed herein.

Any one of the aspects/features/embodiments in combination with any one or more other aspects/features/embodiments.

Use of any one or more of the aspects or features as disclosed herein.

It is to be appreciated that any feature described herein can be claimed in combination with any other feature(s) as described herein, regardless of whether the features come from the same described embodiment.

The details of one or more aspects of the disclosure are set forth in the accompanying drawings and the description below. Other features, objects, and advantages of the techniques described in this disclosure will be apparent from the description and drawings, and from the claims.

The phrases "at least one", "one or more", and "and/or" are open-ended expressions that are both conjunctive and disjunctive in operation. For example, each of the expressions "at least one of A, B and C", "at least one of A, B, or C", "one or more of A, B, and C", "one or more of A, B, or C" and "A, B, and/or C" means A alone, B alone, C alone, A and B together, A and C together, B and C together, or A, B and C together. When each one of A, B, and C in the above expressions refers to an element, such as X, Y, and Z, or class of elements, such as $X_1$-$X_n$, $Y_1$-$Y_m$, and $Z_1$-$Z_o$, the phrase is intended to refer to a single element selected from X, Y, and Z, a combination of elements selected from the same class (e.g., $X_1$ and $X_2$) as well as a combination of elements selected from two or more classes (e.g., $Y_1$ and $Z_o$).

The term "a" or "an" entity refers to one or more of that entity. As such, the terms "a" (or "an"), "one or more" and "at least one" can be used interchangeably herein. It is also to be noted that the terms "comprising", "including", and "having" can be used interchangeably.

The preceding is a simplified summary of the disclosure to provide an understanding of some aspects of the disclosure. This summary is neither an extensive nor exhaustive overview of the disclosure and its various aspects, embodiments, and configurations. It is intended neither to identify key or critical elements of the disclosure nor to delineate the scope of the disclosure but to present selected concepts of the disclosure in a simplified form as an introduction to the more detailed description presented below. As will be appreciated, other aspects, embodiments, and configurations of the disclosure are possible utilizing, alone or in combination, one or more of the features set forth above or described in detail below.

Numerous additional features and advantages of the present invention will become apparent to those skilled in the art upon consideration of the embodiment descriptions provided hereinbelow.

BRIEF DESCRIPTION OF THE DRAWINGS

The accompanying drawings are incorporated into and form a part of the specification to illustrate several examples of the present disclosure. These drawings, together with the description, explain the principles of the disclosure. The drawings simply illustrate preferred and alternative examples of how the disclosure can be made and used and are not to be construed as limiting the disclosure to only the illustrated and described examples. Further features and advantages will become apparent from the following, more detailed, description of the various aspects, embodiments, and configurations of the disclosure, as illustrated by the drawings referenced below.

DETAILED DESCRIPTION

Figure 1:
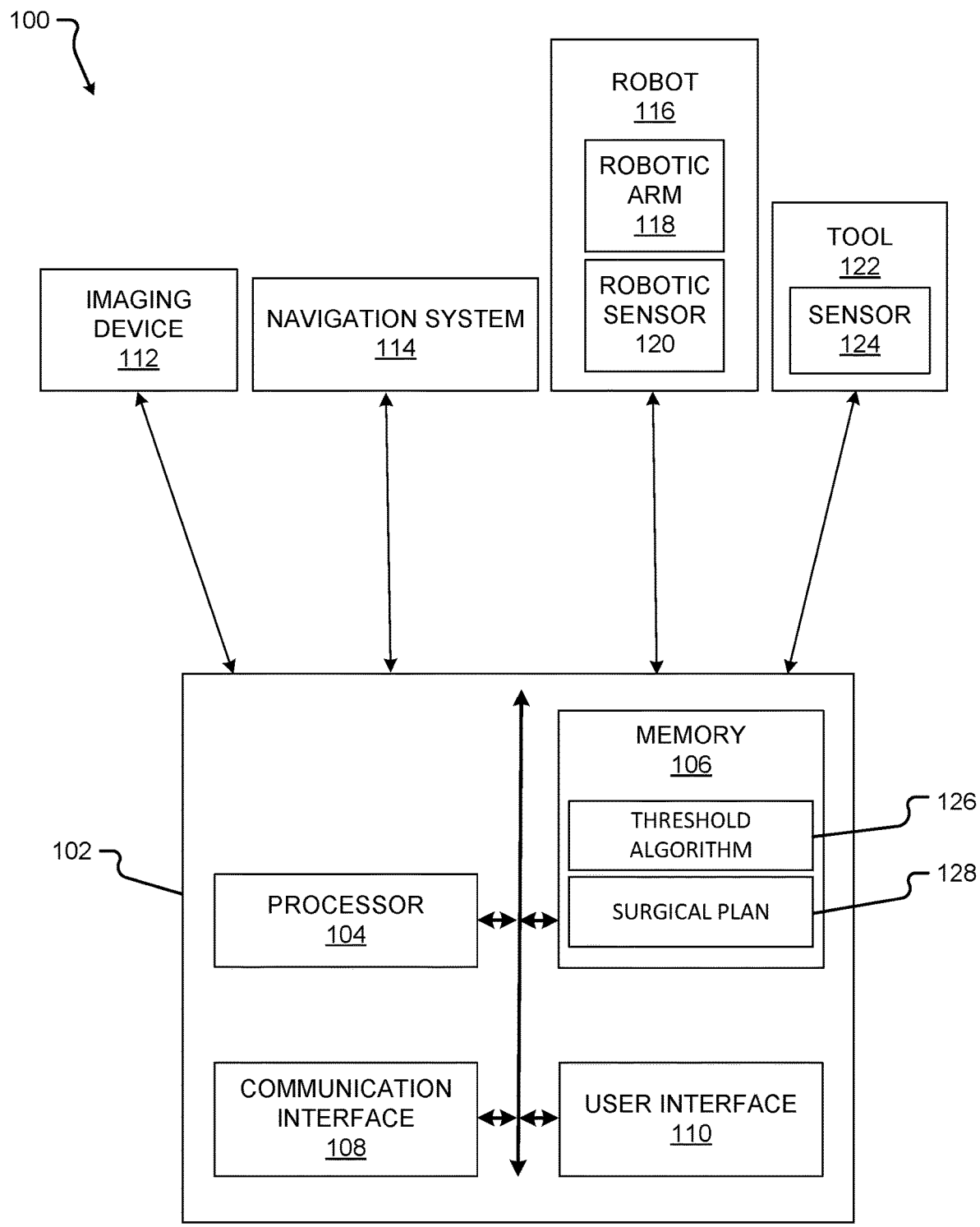
FIG. 1 is a block diagram of a system according to at least one embodiment of the present disclosure.

It should be understood that various aspects disclosed herein may be combined in different combinations than the combinations specifically presented in the description and accompanying drawings. It should also be understood that, depending on the example or embodiment, certain acts or events of any of the processes or methods described herein may be performed in a different sequence, and/or may be added, merged, or left out altogether (e.g., all described acts or events may not be necessary to carry out the disclosed techniques according to different embodiments of the present disclosure). In addition, while certain aspects of this disclosure are described as being performed by a single module or unit for purposes of clarity, it should be understood that the techniques of this disclosure may be performed by a combination of units or modules associated with, for example, a computing device and/or a medical device.

In one or more examples, the described methods, processes, and techniques may be implemented in hardware, software, firmware, or any combination thereof. If implemented in software, the functions may be stored as one or more instructions or code on a computer-readable medium and executed by a hardware-based processing unit. Computer-readable media may include non-transitory computer-readable media, which corresponds to a tangible medium such as data storage media (e.g., RAM, ROM, EEPROM, flash memory, or any other medium that can be used to store desired program code in the form of instructions or data structures and that can be accessed by a computer).

Instructions may be executed by one or more processors, such as one or more digital signal processors (DSPs), general purpose microprocessors (e.g., Intel Core i3, i5, i7, or i9 processors; Intel Celeron processors; Intel Xeon processors; Intel Pentium processors; AMD Ryzen processors; AMD Athlon processors; AMD Phenom processors; Apple A10 or 10x Fusion processors; Apple A11, A12, A12X, A12Z, or A13 Bionic processors; or any other general purpose microprocessors), graphics processing units (e.g., Nvidia GeForce RTX 2000-series processors, Nvidia GeForce RTX 3000-series processors, AMD Radeon RX 5000-series processors, AMD Radeon RX 6000-series processors, or any other graphics processing units), application specific integrated circuits (ASICs), field programmable logic arrays (FPGAs), or other equivalent integrated or discrete logic circuitry. Accordingly, the term "processor" as used herein may refer to any of the foregoing structure or any other physical structure suitable for implementation of the described techniques. Also, the techniques could be fully implemented in one or more circuits or logic elements.

Before any embodiments of the disclosure are explained in detail, it is to be understood that the disclosure is not limited in its application to the details of construction and the arrangement of components set forth in the following description or illustrated in the drawings. The disclosure is capable of other embodiments and of being practiced or of being carried out in various ways. Also, it is to be understood that the phraseology and terminology used herein is for the purpose of description and should not be regarded as limiting. The use of "including," "comprising," or "having" and variations thereof herein is meant to encompass the items listed thereafter and equivalents thereof as well as additional items. Further, the present disclosure may use examples to illustrate one or more aspects thereof. Unless explicitly stated otherwise, the use or listing of one or more examples (which may be denoted by "for example," "by way of example," "e.g.," "such as," or similar language) is not intended to and does not limit the scope of the present disclosure.

In spine surgery with instrumentation such as screws and rods, a surgeon will insert each screw into a corresponding vertebra and connect the screws with a rod. When fixating two or more vertebrae, the rod connecting the screws is meant to align with the geometry of the screw tulip or head. In order to achieve this, the surgeon may need to re-shape the rod and/or force the rod into place. By forcing the rod into place, the surgeon will apply forces onto the screws and may subject the screw to pullout forces and/or potentially break one or more screws (or the pedicles or other vertebral anatomy into which the screws have been placed). The surgeon will also apply forces onto the rod, which may also potentially break the rod or bend the rod into a less effective configuration. These issues are especially problematic when operating on a long construct or using the rod as a tool to achieve alignment (e.g., the surgeon may force the spine to match the geometry of the rod).

Embodiments of the present disclosure provide for a tool used to couple the rod to the tulip. The tool includes an integrated force sensor to measure the forces and/or torques applied onto the screw. The force(s) and/or torque(s) may be examined in real-time by a computerized model that will take into consideration the quality of the screw inserted, the geometry and mechanical properties of the rod, and the patient alignment plan. When inserting the screw robotically, the position of the screws and the geometry of the rod is well defined and known to the robot. Furthermore, the quality of the screw is determined by the robotic arm as the robotic arm inserts the screw via measurement of the force and/or torque when inserting the screw into the spine.

In some embodiments, the tool can be a persuader and can aid in optimizing the rod insertion for an outcome of fitting the rod to the spine (or vice versa) with minimal disruptive forces of the spine and screws. The tool may be handheld and operated by a user (e.g., a surgeon), may be handheld and operated by a user assisted by a robotic system, or may be supported and operated by a robotic system. Sensors on or integrated to the persuader can verify that the forces or torques will not exceed a maximum force or torque that can loosen a screw or break the screw, rod, or hard tissue anatomy. The persuader can instruct the robotic system or user to move from screw to screw to distribute the load and avoid "point loading" a single screw, in a way that takes into account the quality of the screw and will not damage the fixation. In some cases, a robotic system can insert the rod and close the screws. In other cases, a surgeon or user can insert the rod and the system can close the screws. In some embodiments the persuader can be a hand-held device.

As described more fully below, methods, systems, and devices for monitoring a rod reduction process may beneficially prevent breakage or loosening of pedicle screw(s) and/or the rod. By monitoring forces or torques applied during the rod reduction process, the system can detect when the applied force or torque may cause breakage or loosening of the pedicle screw(s) and/or the rod and can cause the system to pause or remove the applied force or applied torque. Further, a surgical plan may be updated to prevent such breakage or loosening of the screw(s) and/or the rod. As such, the rod reduction process may be executed without risk of breaking or loosening pedicle screw(s) and/or a rod.

Embodiments of the present disclosure provide technical solutions to the problems of (1) improving rod reduction processes; (2) monitoring forces or torques exerted on components of a rod reduction process; (3) preventing breakage or loosening of components of a rod reduction process; and/or (4) increasing patient safety during rod reduction processes.

Turning first to FIG. 1, a block diagram of a system 100 according to at least one embodiment of the present disclosure is shown. The system 100 may be used to process image data; execute a threshold algorithm 126; and/or carry out other aspects of one or more of the methods disclosed herein. The system 100 comprises a computing device 102, one or more imaging devices 112, a navigation system 114, a robot 116, a robotic arm 118, one or more robotic sensors 120, one or more tools 122, and/or one or more sensors 124. Systems according to other embodiments of the present disclosure may comprise more or fewer components than the system 100. For example, the system 100 may not include the navigation system 114, the robot 116, the robotic arm 118, the robotic sensor 120, and/or the sensor 124. Systems according to other embodiments of the present disclosure may also be arranged differently than as shown in FIG. 1. For example, the such systems may comprise a tool 122, a sensor 124, and a computing device 102 all enclosed within a common housing.

The computing device 102 comprises a processor 104, a memory 106, a communication interface 108, and a user interface 110. Computing devices according to other embodiments of the present disclosure may comprise more or fewer components than the computing device 102.

The processor 104 of the computing device 102 may be any processor described herein or any similar processor. The processor 104 may be configured to execute instructions stored in the memory 106, which instructions may cause the processor 104 to carry out one or more computing steps utilizing or based on data received from the imaging device 112, the robot 116, the navigation system 114, the robotic sensor 120, the tool 122, and/or the sensor 124.

The memory 106 may be or comprise RAM, DRAM, SDRAM, other solid-state memory, any memory described herein, or any other tangible, non-transitory memory for storing computer-readable data and/or instructions. The memory 106 may store information or data useful for completing, for example, any step of the method 300 described herein. The memory 106 may store, for example, one or more threshold algorithms 126 and/or one or more surgical plans 128. Such algorithms may, in some embodiments, be organized into one or more applications, modules, packages, layers, or engines. The algorithms may cause the processor 104 to manipulate data stored in the memory 106 and/or received from the imaging device 112, the robot 116, the navigation system 114, the robotic sensor 120, the tool 122, and/or the sensors 124.

The computing device 102 may also comprise a communication interface 108. The communication interface 108 may be used for receiving image data or other information from an external source (such as the imaging device 112, the navigation system 114, the robot 116, the robotic sensor 120, the tool 122, and/or the sensors 124), and/or for transmitting instructions, images, or other information to an external system or device (e.g., another computing device 102, the navigation system 114, the imaging device 112, the robot 116, the robotic sensor 120, the tool 122, and/or the sensors 124). The communication interface 108 may comprise one or more wired interfaces (e.g., a USB port, an Ethernet port, a Firewire port) and/or one or more wireless interfaces (configured, for example, to transmit information via one or more wireless communication protocols such as 802.11a/b/g/n, Bluetooth, NFC, ZigBee, and so forth). In some embodiments, the communication interface 108 may be useful for enabling the device 102 to communicate with one or more other processors 104 or computing devices 102, whether to reduce the time needed to accomplish a computing-intensive task or for any other reason.

The computing device 102 may also comprise one or more user interfaces 110. The user interface 110 may be or comprise a keyboard, mouse, trackball, monitor, television, touchscreen, headset, and/or any other device for receiving information from a user and/or for providing information to a user. In some embodiments, the user interface 110 may receive information and/or commands from a user via voice activation. In other embodiments, the user interface 110 may incorporate augmented reality or virtual reality. The user interface 110 may be used, for example, to receive a user selection or other user input regarding receiving a surgical plan 128 for reducing a rod; to receive a user selection or other user input regarding determining, based on at least one parameter, a threshold for forces or torques exerted by a tool 122 on the rod or a pedicle screw; to receive a user selection or other user input regarding causing at least one sensor 124 to monitor a magnitude of the forces or torques exerted by the tool 122 on the pedicle screw or the rod during reduction of the rod into the head; to receive a user selection or other user input regarding updating the plan 128 when the monitored magnitude meets the threshold; to receive a user selection or other user input regarding causing a robotic arm 118 to insert the rod into the patient; to receive a user selection or other user input regarding causing the robotic arm 118 to operate the tool 122 to reduce the rod onto a plurality of pedicle screws in stages, the plurality of pedicle screws including the pedicle screw; to receive a user selection or other user input regarding receiving, from at least one robotic sensor 120, sensor data corresponding to a force or torque exerted by the robotic arm 118 onto the pedicle screw during implantation of the pedicle screw in the patient; to receive a user selection or other user input regarding determining a screw quality of the pedicle screw based on the sensor data; and/or to display images and/or a surgical plan 128. In some embodiments, the user interface 110 may be useful to allow a surgeon or other user to modify a plan 128, or other information displayed, though it will be appreciated that each of the preceding inputs may be generated automatically by the system 100 (e.g., by the processor 104 or another component of the system 100) or received by the system 100 from a source external to the system 100. In some embodiments, user input such as that described above may be optional or not needed for operation of the systems, devices, and methods described herein.

Although the user interface 110 is shown as part of the computing device 102, in some embodiments, the computing device 102 may utilize a user interface 110 that is housed separately from one or more remaining components of the computing device 102. In some embodiments, the user interface 110 may be located proximate one or more other components of the computing device 102, while in other embodiments, the user interface 110 may be located remotely from one or more other components of the computer device 102.

The imaging device 112 may be capable of taking a 2D image or a 3D image to yield an image and/or image data. The imaging device 112 may be used to verify or monitor placement of the tool 122 and/or a surgical instrument (e.g., pedicle screw(s) and/or rod). "Image data" as used herein refers to the data generated or captured by an imaging device, including in a machine-readable form, a graphical form, and in any other form. The imaging device 112 may be or comprise, for example, a camera, a CT scanner, a fluoroscope, an ultrasound probe, an O-arm, a C-arm, a G-arm, any other device utilizing X-ray-based imaging, a magnetic resonance imaging (MRI) scanner, an optical coherence tomography scanner, an endoscope, a microscope, a thermographic camera (e.g., an infrared camera), or any other imaging device suitable for obtaining images or image data corresponding to an anatomical feature of a patient or an object.

The navigation system 114 may provide navigation for a surgeon and/or a surgical robot during an operation. The navigation system 114 may be any now-known or future-developed navigation system, including, for example, the Medtronic StealthStation™ S8 surgical navigation system. The navigation system 114 may include a camera or other sensor(s) for tracking one or more reference markers or other objects within the operating room or other room where a surgery takes place. In various embodiments, the navigation system 114 may be used to track a position of the imaging device 112 (or, more particularly, of a navigated reference marker attached, directly or indirectly, in fixed relation to the imaging device 112) and/or of the robot 116 (or, more particularly, of a navigated reference marker attached, directly or indirectly, in fixed relation to the robot 116). The navigation system 114 may include a display for displaying one or more images from an external source (e.g., the computing device 102, imaging device 112, or other source) or a video stream from the camera or other sensor of the navigation system 114. In some embodiments, the system 100 can operate without the use of navigation system 114.

The robot 116 may be any surgical robot or surgical robotic system. The robot 116 may be or comprise, for example, the Mazor X™ Stealth Edition robotic guidance system. The robot 116 may comprise one or more robotic arms 118. In some embodiments, the robotic arm 118 may comprise a plurality of robotic arms, though the robot 116 may comprise one robotic arm, two robotic arms, or more than two robotic arms. The robotic arm 118 may be used to selectively hold and/or operate one or more imaging devices 112, the tool 122, and/or any instrument (e.g., pedicle screws, set screws, and/or rods). In some embodiments, the robotic arm 118 has at least five degrees of freedom. In other embodiments, the robotic arm 118 has at least six degrees of freedom. In yet other embodiments, the robotic arm 118 has fewer than five or greater than six degrees of freedom. The robotic arm 118 (and/or a base of the robot 116) may also have three dimensions of orientation. The combination of multiple degrees of freedom and multiple dimensions of orientation allows for the robotic arm 118 to move to any pose. In other words, the robotic arm 118 is not limited to a fixed area and can move in any direction. Further, in some embodiments, the robot 116 can move during a surgical procedure to position the robotic arm 118 (and thus, the tool 122).

Reference markers (e.g., navigation markers) may be placed on the robot 116, the robotic arm 118, the imaging device 112, the tool 122, and/or any other object in the surgical space. The markers may be tracked by the navigation system 114, and the results of the tracking may be used by the robot 116 and/or by an operator of the system 100 or any component thereof. As described above, in some embodiments, the navigation system 114 can be used to track other components of the system 100 (e.g., the imaging device 112) and the system 100 can operate without the use of the robot 116 (e.g., with the surgeon manually manipulating the imaging device 112).

In some embodiments, the robot 116 comprises the one or more robotic sensors 120 operable to yield sensor data of the robot 116 or the robotic arm 118. In alternative embodiments, the robot 116 does not comprise the robotic sensors 120. The sensor data may include, but is not limited to, a force or torque experienced by the robotic arm 118 and/or the robot 116. In some examples, the force or torque corresponds to a force or torque received by a surgical instrument (e.g., a pedicle screw) from the robotic arm 118.

In such examples, the sensor data may be used to determine a change in a mechanical property of the surgical instrument.

Each robotic sensor 120 may be any kind of robotic sensor 120 for measuring the force or torque. The robotic sensor 120 may include one or more or any combination of components that are electrical, mechanical, electro-mechanical, magnetic, electromagnetic, or the like. The robotic sensor 120 may include, but is not limited to, one or more of a torque sensor, a force sensor, a linear encoder, a rotary encoder, a capacitor, and/or an accelerometer. In some embodiments, the robotic sensor 120 may include a memory for storing sensor data. In still other examples, the robotic sensor 120 may output signals (e.g., sensor data) to one or more sources (e.g., the computing device 102, the navigation system 114, and/or the robot 116).

The robotic sensor 120 may be integrated internally into the robotic arm 118 or otherwise positioned inside of the robotic arm 118. In some embodiments, the robotic sensor 120 is positioned inside a joint (shown in FIG. 2) of the robotic arm 118. The robotic sensor 120 may include a plurality of sensors and each sensor may be positioned at the same location or a different location as any other sensor. For example, a robotic sensor 120 may be positioned in one or more joints of the robotic arm 118. It will be appreciated that in some embodiments the sensor(s) 120 can be positioned at or on any component of the system 100 or surrounding environment (e.g., on any portion of the navigation system 114, the robot 116, the robotic arm 118, and/or any other component at the surgical site).

In some embodiments, the robotic sensor 120 may send data to the computing device 102 to display on the user interface 110 or otherwise notify the surgeon or operator of the sensor data received from the robotic sensor 120. In other embodiments, the robotic sensor 120 may alert the surgeon or operator of a change in a mechanical property of the surgical instrument (e.g., a pedicle screw) by an alert such as a sound or a light display.

The tool 122 may enable execution of a surgical procedure such as a rod reduction. The tool 122 can be hand-held or adapted to be held by the robotic arm 118. In some embodiments, the tool 122 is used manually by a user (e.g., a surgeon). For example, the tool 112 may be used by a user to persuade a rod into place while also gauging forces applied to a pedicle screw to which the rod is being persuaded. In other words, a physical connection between the tool 112 and the screw may not be robotically controlled. In other embodiments, the robot 116 may aid the surgeon in using the tool 122. In further embodiments, the tool 122 may be held by the robotic arm 118 and automatically controlled by the robot 116. Instructions for using the tool 122 may either be machine readable or human readable. In examples where the instructions are machine readable, the instructions may be transmitted to the robot 116 to execute. In examples where the instructions are human readable, the instructions may be displayed on the user interface 110 or audibly communicated to the surgeon.

In some embodiments, the tool 122 is a persuader for reducing a rod onto one or more heads of one or more pedicle screws. In other embodiments, the tool 122 may be any tool used during a rod reducing process. For example, the tool 122 may be either a screwdriver for driving a pedicle screw into a vertebra, a pedicle screw extender for gripping the pedicle screw at an extended distance, and/or a nut driver for tightening a set screw into a head of a pedicle screw.

Sensor(s) 124 may be used to track and/or sense a force or torque exerted by the tool 122 on a surgical instrument (e.g., a rod and/or pedicle screw(s)). In some embodiments, the sensor 124 is disposed on the tool 122. In other embodiments, the sensor 124 is disposed on a head of a pedicle screw. In further embodiments, the sensor 124 may be positioned on any component of the system 100. The sensor 124 may be any kind of sensor 124 for measuring the force or torque exerted by the tool 122. The sensor 124 may include one or more or any combination of components that are electrical, mechanical, electro-mechanical, magnetic, electromagnetic, or the like. The sensor 124 may include, but is not limited to, one or more of a torque sensor, a force sensor, a linear encoder, a rotary encoder, a capacitor, and/or an accelerometer. In some embodiments, the sensor 124 may include a memory for storing sensor data. In still other examples, the sensor 124 may output signals (e.g., sensor data) to one or more sources (e.g., the computing device 102, the navigation system 114, and/or the robot 116). The sensor 124 may be either positioned adjacent to or integrated with the tool 122. The sensor 124 may include a plurality of sensors and each sensor may be positioned at the same location or a different location as any other sensor.

In some embodiments, the sensor 124 may send the data to the computing device 102 when the sensor 124 detects that a magnitude of the forces or torques exerted by the tool 122 exceeds a threshold. In other embodiments, the sensor 124 may continuously send the data to the computing device 102. Further, in some embodiments, the sensor 124 may send data to the computing device 102 to display on the user interface 110 or otherwise notify the surgeon or operator of the magnitude exceeding the threshold. In other embodiments, the sensor 124 may alert the surgeon or operator of the magnitude exceeding the threshold by an alert such as a sound or a light display. The sensor 124 may advantageously provide a safety function by monitoring and alerting the surgeon or operator of the magnitude exceeding the threshold.

Figure 2:
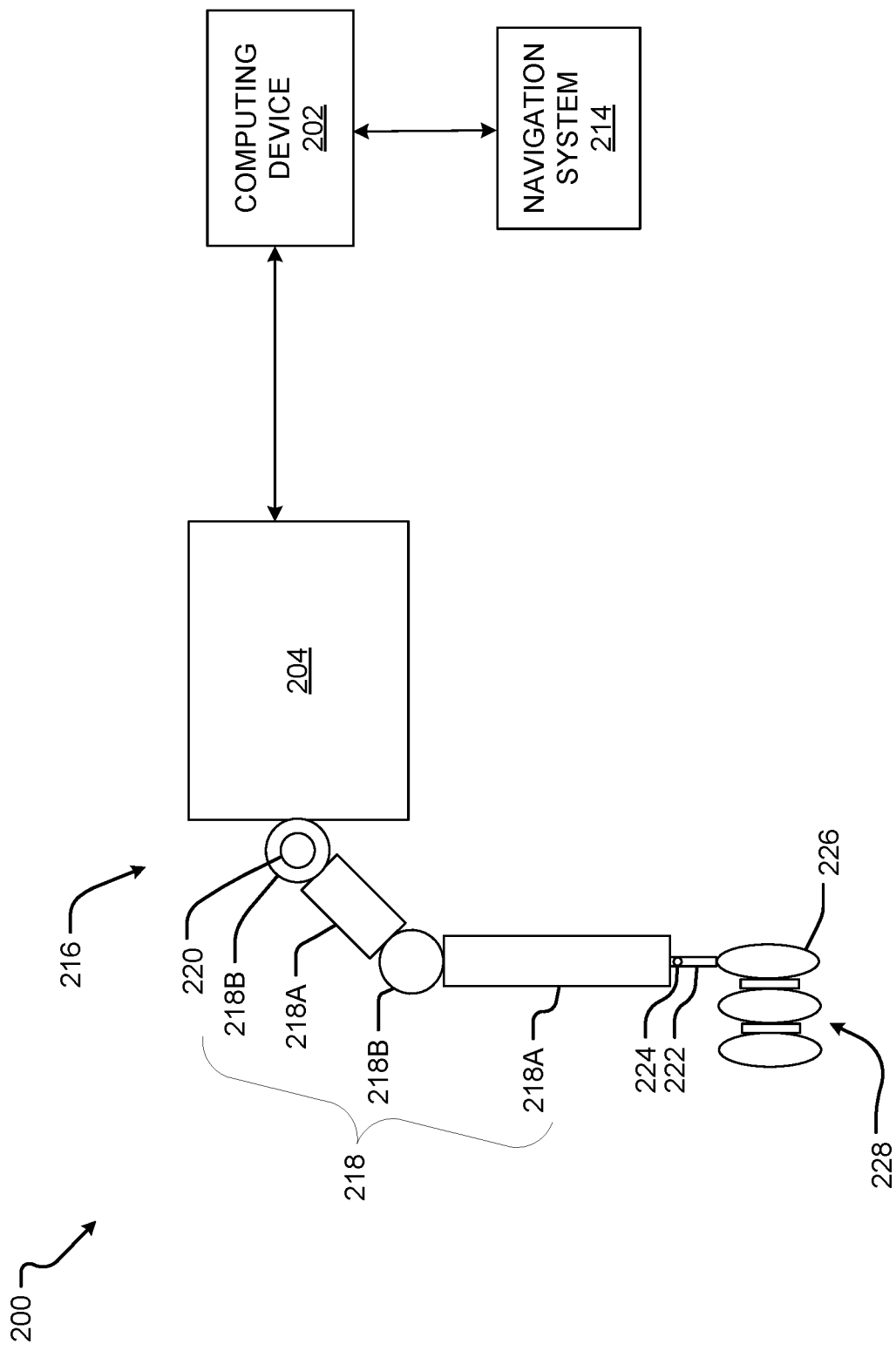
FIG. 2 is a diagram of a system according to at least one embodiment of the present disclosure.

Turning to FIG. 2, a block diagram of another system 200 according to at least one embodiment of the present disclosure is shown. The system 200 includes a computing device 202 (which may be the same as or similar to the computing device 102 described above), a navigation system 214 (which may be the same as or similar to the navigation system 114 described above), and a robot 216 (which may be the same as or similar to the robot 116 described above). Systems according to other embodiments of the present disclosure may comprise more or fewer components than the system 200. For example, the system 200 may not include the navigation system 214.

As illustrated, the robot 216 includes a robotic arm 218 (which may comprise one or more members 218A connected by one or more joints 218B) extending from a base 204. In other embodiments, the robot 216 may include two or more robotic arms. The base 204 may be stationary or movable. The robotic arm 218 is operable to execute one or more planned movements and/or procedures autonomously and/or based on input from a surgeon or operator. In the illustrated embodiment, a tool 222 (which may be the same as or similar to the tool 122 described above), may be disposed at an end of the robotic arm 218, though the tool 222 (or any other tool(s) or instrument(s)) may be disposed on any portion of the robotic arm 218. In other embodiments, the tool 222 may be handheld and operated by a user or by a user assisted by the robot 216. The tool 222 may be used to perform a procedure on a vertebra 226 of a spinal region 228. Further, different tools 222 may be attached to the robotic arm 218 at difference stages of a surgical procedure. For example, a drill may be attached to the robotic arm 218 to drill a hole for a pedicle screw, and a screwdriver may then be attached to the robotic arm 218 to drive the pedicle screw in the hole. In the same example, a driver may be attached to the robotic arm 218 to drive a set screw in a head of each pedicle screw.

A robotic sensor 220 (which may be the same as or similar to the robotic sensor 120 described above, and of which more than one may be included in the robotic arm 218) may be integrated into a joint 218B of the robotic arm 218. Though the sensor 220 is shown integrated into the joint 218B nearest the base 204, the sensor 220 may be integrated into any joint 218B, any member 218A, or any portion of the robotic arm 218 and/or the robot 216. Furthermore, more than one robotic sensor 220 may be integrated into the robotic arm 218 and/or the robot 216. As similarly described above, the robotic sensor 220 may be one or more of a torque sensor, a force sensor, or an encoder integrated into the joint 218B. The robotic sensor 220 is configured to sense at least one of an applied force or an applied torque exerted on the robotic arm 218. As will be described below with respect to FIG. 3, such sensor data may be used to determine a screw quality of each of one or more pedicle screws.

A sensor 224 (which may either be the same as or similar to the sensor 224 described above) may also be integrated into the tool 222. As described above, the sensor 224 may be disposed on the tool 222, and may be used to track and/or sense a force or torque exerted by the tool 122 on a surgical instrument (e.g., a rod and/or pedicle screw(s)), or vice versa. The sensor 224 may also be integrated into the tool 122. The sensor 124 may be any kind of sensor 124 for measuring the force or the torque exerted by the tool 222 on a pedicle screw or other surgical instrument or device, or vice versa.

Figure 3:
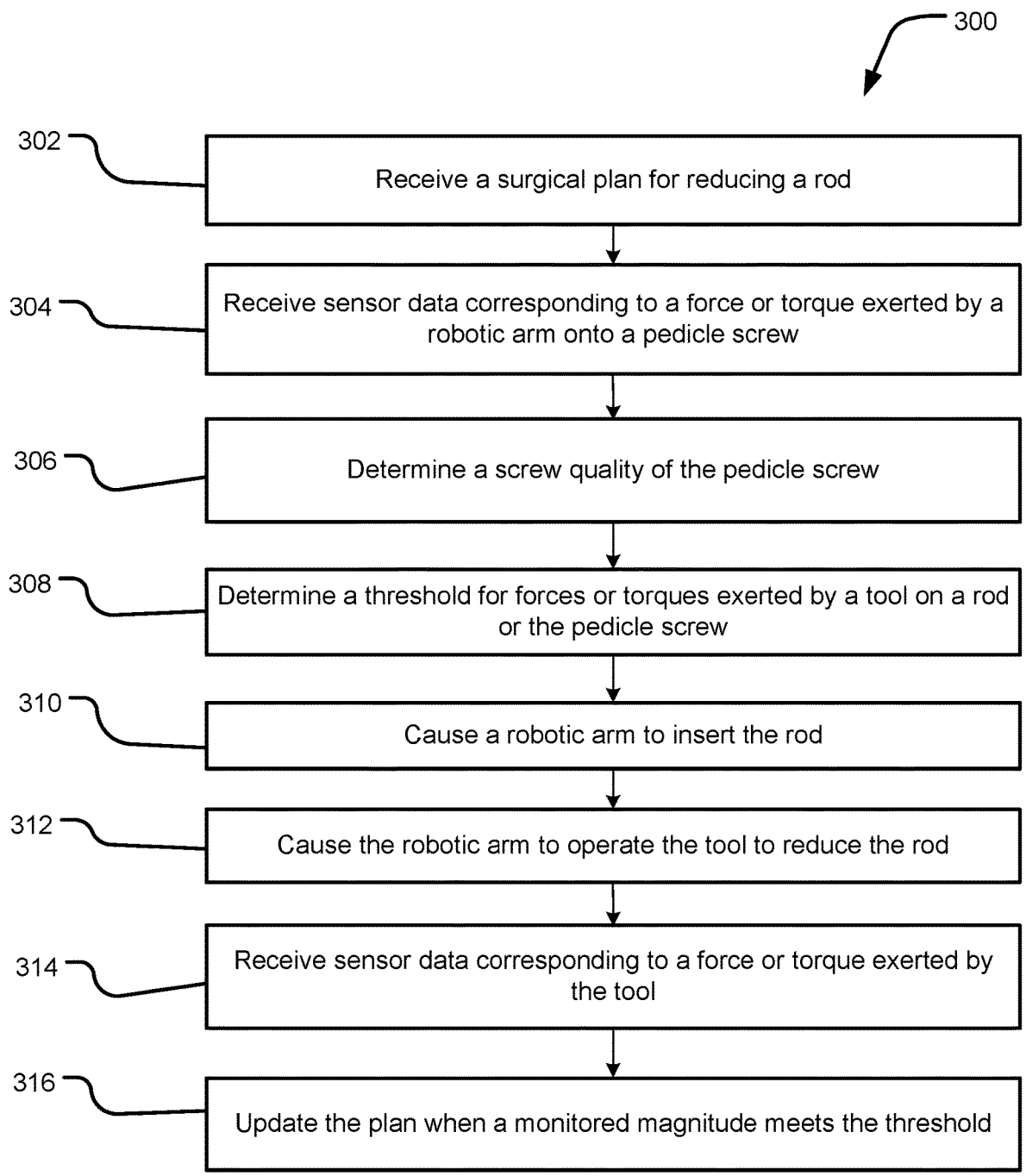
FIG. 3 is a flowchart of a method according to at least one embodiment of the present disclosure.

Turning now to FIG. 3, a method 300 for monitoring a rod reduction process may be carried out or otherwise performed, for example, by at least one processor. The at least one processor may be the same as or similar to the processor(s) 104 of the computing device 102 or 202 described above. The at least one processor may be part of a robot (such as a robot 116 or 216) or part of a navigation system (such as a navigation system 114 or 214). A processor other than any processor described herein may also be used to execute the method 300. The at least one processor may perform the method 300 by executing instructions stored in a memory (such as the memory 106). The instructions may correspond to one or more steps of the method 300 described below. One or more aspects of the method 300 may be performed by or with a surgical robot and/or a surgeon.

The method 300 comprises receiving a surgical plan such as the surgical plan 128 for reducing a rod (step 302). The surgical plan may be received via a user interface (e.g., the user interface 110) and/or a communication interface (e.g., the communication interface 108) of a computing device such as the computing device 102 or 202, and may be stored in a memory such as the memory 106 of the computing device. The surgical plan may include information about a rod reduction process. The information may include a pedicle screw placement, a rod shape, a rod insertion point, an order in which a rod will be reduced onto a plurality of pedicle screws, and/or an amount of force or torque exerted for each rod reduction step. The surgical plan may also include information about one or more planned movements of a robotic arm such as the robotic arm 118 or 218. In some embodiments, the surgical plan includes a planned trajectory or path for the robotic arm.

The method 300 may also comprise receiving sensor data corresponding to a force or torque exerted onto the pedicle screw during implantation of the pedicle screw in the patient (step 304). The force or torque exerted may be force or torque exerted by a robotic arm or by a user operating a tool such as the tool 122 or 222. The sensor data may be obtained from at least one sensor such as the sensor 124 or 224 disposed on or integrated with a tool such as the tool 122 or 222 or from at least one robotic sensor such as the robotic sensor 120 or 220 on a robotic arm such as the robotic arm 118 or 218. The at least one robotic sensor may either be positioned on the robotic arm or integrated with the robotic arm. The robotic sensor may send data to the computing device to display on the user interface. A processor such as the processor 104 or any other component of the system such as the system 100 or 200 may receive the sensor data and generate a notification to notify the surgeon or operator of the sensor data received from the robotic sensor. In other embodiments, the processor or other component of the system may alert the surgeon or operator of a change in a mechanical property (described below in step 306) of the surgical instrument (e.g., a pedicle screw) by an alert such as a sound or a light display.

The method 300 also comprises determining a screw quality of the pedicle screw (step 306). The determining may be based on sensor data received in step 304. The sensor data may be a force and/or a torque exerted by the robotic arm onto the pedicle screw (and thus, corresponding to the force and/or torque received by the pedicle screw) when the screw is inserted into a vertebra. Determining the screw quality may include calculating a change in one or more mechanical properties of each screw as a result of the force or torque received by each screw. For example, a screw may experience a change in stress due to a force or torque received from the robotic arm. In the same example, if the change in stress is greater than a maximum stress of the screw, then the screw may subsequently no longer be able to withstand the same amount of force or torque initially received. Thus, the threshold may be decreased to avoid applying a force or torque equal to or near the force or torque initially received. The screw quality may also be determined based on sensed sound and/or vibration(s) data corresponding to the screw during insertion of the screw. The sound and/or vibration data may provide further information about a change in one or more mechanical properties of the screw.

The method 300 also comprises determining, based on at least one parameter, a threshold for forces or torques exerted by a tool such as the tool 122 or 222 on the rod or a pedicle screw (step 308). The determining may comprise executing a threshold algorithm such as the threshold algorithm 126. The threshold may be set at a level that will prevent (at some level of statistical certainty, for example) the tool from exerting a force or torque that will break the rod, the pedicle screw, and/or corresponding vertebrae during the rod reduction. Determining this threshold may include determining and analyzing bone quality of corresponding vertebrae to avoid breaking any of the corresponding vertebrae. Further, the threshold may be set at a level that will prevent (again, for example, at some level of statistical certainty) the tool from exerting a force or torque that will pull the pedicle screw out of a vertebra.

The at least one parameter may be received by the computing device, and more particularly, by the processor of the computing device, and may be stored in the memory. In some embodiments, the at least one parameter may be indirectly received via any other component of the system or a node of a network to which the system is connected. The at least one parameter may also be received from a surgical plan such as the surgical plan 128. The at least one parameter may also be, but is not limited to, a screw quality, a geometry of the rod, a mechanical property of the rod, a rod strength analysis, an updated spine position, a bone quality, one or more dimensions of the bone into which the screw has been screwed, a patient age, and/or a patient range of motion.

Where the at least one parameter includes screw quality, the screw quality may be determined from sensor data (such as force data or torque data) as detected by a robotic sensor (such as the robotic sensor 120 or 220) as described with respect to step 306. The sensor data may be obtained as described with respect to step 304, described above. For example, a strength of the screw may be reduced if the screw receives a force or torque greater than an anticipated force or torque during insertion of the screw. Where the at least one parameter includes bone quality, the bone quality may be obtained from preoperative image(s) and/or patient input.

Any one or more of the geometry, mechanical property, and/or rod strength of the rod, when included in the at least one parameter, may be received from a surgical plan (e.g., a surgical plan 128) that includes dimensions and the geometry of the rod. The geometry, mechanical property, and/or rod strength of the rod may also be received from a surgeon. Such information may be received, for example, via a user interface such as the user interface 110 and/or a communication interface such as the communication interface 108 of the computing device. The mechanical property of the rod may include, but is not limited to, at least one of hardness, brittleness, ductility, toughness, and/or strength.

The updated spine position of a patient may be received from the surgical plan or input received from a surgeon. The input may be received, for example, via the user interface and/or the communication interface of the computing device. The updated spine position may also be depicted in or otherwise determinable from an image of the patient prior to or during a surgical procedure received from an imaging device, such as the imaging device 112.

The patient range of motion may be input received from a surgeon or patient. The input may be received, for example, via the user interface and/or the communication interface of the computing device. The patient range of motion may include, but is not limited to, a range of motion of a spinal region of the patient. The range of motion may be determined, in some embodiments, by a computing device such as the computing device 102 or 202, based on a plurality of images showing the patient in positions of maximum bending (e.g., positions of flexion or extension).

The method 300 further comprises inserting the rod into a patient (step 310). The rod may be inserted by a robotic arm such as the robotic arm 118 or 218, in which case the step 310 comprises causing the robotic arm to insert the rod into the patient. Alternatively, the rod may be inserted by a user (based, for example, on instructions provided via a user interface), or may be inserted by a user assisted by a robot such as the robot 116 or 216. In some embodiments, the robotic arm may insert the rod based on an insertion point and/or trajectory defined by the surgical plan. In other embodiments, the robotic arm may insert the rod based on inputs received from a surgeon or user. The input may be received, for example, via a user interface such as the user interface 110 and/or a communication interface such as the communication interface 108 of a computing device such as the computing device 102 or 202.

The method 300 also comprises operating the tool to reduce the rod onto a plurality of pedicle screws in stages (step 312). The tool may be operated by a robotic arm such as the robotic arm 118 or 218, in which case the step 312 comprises causing the robotic arm to operate the tool to reduce the rod onto the plurality of screws in stages.

Alternatively, the tool may be operated by a user (e.g., based on instructions provided via a user interface), or may be operated by a user assisted by a robot such as the robot 116 or 216. Reducing the rod in stages is based on the surgical plan and comprises causing the robotic arm or surgeon to incrementally tighten, in sequence, a set screw in a head of each pedicle screw of the plurality of pedicle screws to avoid point loading any single pedicle screw. Reducing the rod in stages may include generating instructions to reduce the rod in stages. In some embodiments, the instructions may be machine readable and transmitted to the robotic arm. In other embodiments, the instructions may be displayed on the user interface or audibly communicated to the surgeon.

The method 300 also comprises receiving sensor data corresponding a magnitude of a force or torque exerted by the tool on the pedicle screw or the rod during reduction of the rod into a head (step 314). The sensor data may be obtained from at least one sensor, which may be or comprise, for example, a sensor 124 or 224. As previously described, the sensor may be used to track and/or sense a force or torque exerted by the tool on a surgical instrument (e.g., a rod and/or pedicle screw(s)). The sensor may be disposed on the tool, on a head of a screw, or on any component of the system. In some embodiments, the sensor is integrated into the tool. The sensor may be any kind of sensor for measuring the force or torque exerted by the tool on the pedicle screw or the rod. The sensor may include one or more or any combination of components that are electrical, mechanical, electro-mechanical, magnetic, electromagnetic, or the like. The sensor may include, but is not limited to, one or more of a torque sensor, a force sensor, a linear encoder, a rotary encoder, a capacitor, and/or an accelerometer. In some embodiments, the sensor may include a memory for storing sensor data. In still other examples, the sensor may output signals to one or more sources (e.g., a computing device such as the computing device 102 or 202, a navigation system such as the navigation system 114 or 214, and/or the robot). The sensor may include a plurality of sensors (which may or may not all be the same as each other) and each sensor may be positioned at the same location or a different location as any other sensor.

In some embodiments, the sensor may send sensed data to the computing device when the sensor detects that a magnitude of the forces or torques exerted by the tool exceeds a threshold, as described further below. In other embodiments, the sensor may continuously send sensed data to the computing device. Further, in some embodiments, the sensor may send data to the computing device to display on the user interface or to otherwise notify the surgeon or operator of the monitored magnitude and/or that the magnitude exceeds the threshold. In other embodiments, based on sensor data, the processor or other component of the system may alert the surgeon or operator of the magnitude exceeding the threshold by an alert such as a sound or a light display. The sensor may advantageously provide a safety function by monitoring and alerting the surgeon or operator of the magnitude exceeding the threshold.

In some embodiments, the sensor may be used to monitor a pose of the robotic arm. In the same embodiments, the sensor may be used to monitor a position of each pedicle screw and a position of the rod via the robotic arm (e.g., one or more robotic arms may be holding or otherwise contacting a pedicle screw or rod). For example, the robotic arm may hold the rod during rod insertion or may hold the pedicle screw during insertion of the pedicle screw. The position of each pedicle screw and the position of the rod may be monitored in real-time. In other embodiments, the position of each pedicle screw and/or the position of the rod is monitoring by the navigation system. In further embodiments, the rod and/or each pedicle screw may be monitored by a robotic sensor such as the robotic sensor 120 or 220.

The method 300 also comprises updating the surgical plan when the monitored magnitude meets the threshold (step 316). The updating may include updating one or more surgical steps of the surgical plan. For example, an order of pedicle screws to reduce may be adjusted. In another example, the threshold may be adjusted. In a further example, one or more surgical steps may be introduced to and/or removed from the plan. For example, the plan may be modified to include more surgical steps to move from pedicle screw to pedicle screw to distribute the force or torque loads and to avoid "point loading" onto a single pedicle screw.

The updating may include updating a position and/or orientation of one or more pedicle screws. For example, the position of one of the pedicle screws may be adjusted to reduce the force or torque on a pedicle screw. In another example, the position of one of the pedicle screws may be adjusted to account for a new rod shape (which the new rod shape may be calculated or otherwise generated to reduce the forces or torques required to reduce the rod to the pedicle screws or vice versa). In yet another example, the position of one of the pedicle screws may be adjusted based on the screw quality as determined in step 306, as previously described.

The updating may also include updating a rod shape, a rod trajectory, and/or a rod insertion point. The rod shape, trajectory and/or insertion point may be updated to reduce the force or torque received by the rod and/or the pedicle screw(s). The rod shape, trajectory and/or insertion point may also be updated to account for a new position and/or a new orientation of one or more pedicle screws.

In some embodiments, the procedure may pause during the updating. For example, the robotic arm may automatically pause or may release a force or torque applied to a pedicle screw and/or rod when the magnitude meets the threshold. In another example, a notification may be audibly or visually communicated to the surgeon to alert the surgeon that the magnitude has met the threshold. In other examples, the robot may not allow the surgeon to complete a surgical step when the threshold has been met.

The methods and systems described herein provide a system, method, and device for monitoring a rod reduction process based on determining a threshold for forces or torques exerted by a tool on a pedicle screw or a rod and monitoring a magnitude of the forces or torques exerted by the tool on the pedicle screw or the rod during the rod reduction process. The monitoring beneficially reduces a likelihood of breakage or loosening of pedicle screw(s), the rod, and/or the patient's vertebrae and/or other bony anatomy. By monitoring forces or torques applied during the rod reduction process, the system detects when the applied force or torque may cause breakage or loosening of the pedicle screw(s), the rod, and/or the patient's bony anatomy, and prevents the tool from applying such force or torque. Further, a surgical plan may be updated during the process to prevent such breakage or loosening of the screw(s) and/or the rod. As such, the rod reduction process may be executed and updated to prevent breaking or loosening pedicle screw(s) and/or a rod.

As may be appreciated based on the foregoing disclosure, the present disclosure encompasses methods with fewer than all of the steps identified in FIG. 3 (and the corresponding description of the method 300), as well as methods that include other and/or additional steps beyond those identified in FIG. 3 (and the corresponding description of the method 300). For example, the method 300 may comprise only one, or only two, of the steps 302 to 316. Methods of the present disclosure explicitly include methods with one or more steps described above as part of the method 300.

The foregoing discussion has been presented for purposes of illustration and description. The foregoing is not intended to limit the disclosure to the form or forms disclosed herein. In the foregoing Detailed Description, for example, various features of the disclosure are grouped together in one or more aspects, embodiments, and/or configurations for the purpose of streamlining the disclosure. The features of the aspects, embodiments, and/or configurations of the disclosure may be combined in alternate aspects, embodiments, and/or configurations other than those discussed above. This method of disclosure is not to be interpreted as reflecting an intention that the claims require more features than are expressly recited in each claim. Rather, as the following claims reflect, inventive aspects lie in less than all features of a single foregoing disclosed aspect, embodiment, and/or configuration. Thus, the following claims are hereby incorporated into this Detailed Description, with each claim standing on its own as a separate preferred embodiment of the disclosure.

Moreover, though the description has included description of one or more aspects, embodiments, and/or configurations and certain variations and modifications, other variations, combinations, and modifications are within the scope of the disclosure, e.g., as may be within the skill and knowledge of those in the art, after understanding the present disclosure. It is intended to obtain rights which include alternative aspects, embodiments, and/or configurations to the extent permitted, including alternate, interchangeable and/or equivalent structures, functions, ranges or steps to those claimed, whether or not such alternate, interchangeable and/or equivalent structures, functions, ranges or steps are disclosed herein, and without intending to publicly dedicate any patentable subject matter.

What is claimed is:

1. A system for monitoring a rod reduction process comprising:
    a tool configured to reduce a rod into a head of a pedicle screw;
    at least one sensor configured to measure forces or torques exerted on the pedicle screw;
    at least one processor; and
    at least one memory storing instructions for execution by the at least one processor that, when executed, cause the at least one processor to:
        determine, based on at least one parameter, a threshold for forces or torques exerted by the tool on the pedicle screw;
        receive, from the at least one sensor, data corresponding to a magnitude of the forces or torques exerted by the tool on the pedicle screw during reduction of the rod into the head by the tool;
        determine a screw quality based on the data received from the at least one sensor by calculating a change in one or more mechanical properties of the pedicle screw as a result of the forces or torques received by the pedicle screw; and
        decrease the threshold when the one or more mechanical properties meets or exceeds one or more corresponding target mechanical properties.

2. The system of claim 1, wherein the tool is handheld and operated by a user.

3. The system of claim 1, wherein the at least one sensor is disposed on at least one of the tool or the head of the pedicle screw.

4. The system of claim 3, wherein the at least one sensor is disposed on the tool and is integrated into the tool.

5. The system of claim 1, wherein the at least one parameter is at least one of a screw quality, a geometry of the rod, a mechanical property of the rod, a patient range of motion, a bone quality, or a preoperative plan.

6. The system of claim 1, wherein the at least one memory stores additional instructions for execution by the at least one processor that, when executed, further cause the at least one processor to:
    update a plan for reducing the rod when the magnitude meets the threshold.

7. The system of claim 1, further comprising:
    at least one robotic arm configured to selectively implant the pedicle screw in a patient and hold the tool; and
    at least one robotic sensor disposed on the robotic arm,
    wherein the at least one memory stores additional instructions for execution by the at least one processor that, when executed, further cause the at least one processor to:
        receive, from the at least one robotic sensor, sensor data corresponding to a force or torque exerted by the robotic arm onto the pedicle screw during implantation of the pedicle screw in the patient.

8. The system of claim 7, wherein the at least one memory stores additional instructions for execution by the at least one processor that, when executed, further cause the at least one processor to:
    cause the robotic arm to insert the rod into the patient.

9. The system of claim 7, wherein the at least one memory stores additional instructions for execution by the at least one processor that, when executed, further cause the at least one processor to:
    cause the robotic arm to operate the tool to reduce the rod onto a plurality of pedicle screws in stages, the plurality of pedicle screws including the pedicle screw.

10. The system of claim 9, wherein reducing the rod in stages comprises causing the robotic arm to incrementally tighten, in sequence, a set screw in a head of each pedicle screw of the plurality of pedicle screws, to avoid point loading any single pedicle screw.

11. The system of claim 1, wherein the tool is a persuader.

12. A device for monitoring a rod reduction process comprising:
    at least one processor; and
    at least one memory storing instructions for execution by the at least one processor that, when executed, cause the at least one processor to:
        determine a threshold, based on at least one parameter, for a force or torque exerted by a rod reduction tool during reduction of a rod into a head of each pedicle screw of one or more pedicle screws;
        receive, from at least one sensor, data corresponding to a magnitude of the force or torque exerted by the rod reduction tool on the one or more pedicle screws during reduction of the rod into the head;
        determine a screw quality based on the data received from the at least one sensor, wherein determining the screw quality includes calculating a change in one or more mechanical properties of each pedicle screw of the one or more pedicle screws as a result of the force or torque received by each pedicle screw of the one or more pedicle screws; and decrease the threshold when the one or more mechanical properties meets or exceeds one or more corresponding target mechanical properties.

13. The device of claim 12, wherein the rod reduction tool is handheld and operated by a user.

14. The device of claim 13, wherein the at least one parameter is at least one of a screw quality, a geometry of the rod, a mechanical property of the rod, a patient range of motion, a bone quality, or a preoperative plan.

15. The device of claim 13, wherein the at least one memory stores additional instructions for execution by the at least one processor that, when executed, further cause the at least one processor to:
  update a plan for reducing the rod when the magnitude meets the threshold.

16. The device of claim 12, wherein the at least one memory stores additional instructions for execution by the at least one processor that, when executed, further cause the at least one processor to:
  cause a robotic arm to insert the rod into a patient.

17. The device of claim 12, wherein the at least one memory stores additional instructions for execution by the at least one processor that, when executed, further cause the at least one processor to:
  cause a robotic arm to operate the rod reduction tool to reduce the rod onto the one or more pedicle screws in stages.

18. The device of claim 17, wherein reducing the rod in stages comprises causing the robotic arm to incrementally tighten, in sequence, a set screw in a head of each pedicle screw of the one or more pedicle screws, to avoid point loading any single pedicle screw.

* * * * *